(12) United States Patent
Dugan et al.

(10) Patent No.: US 10,070,975 B2
(45) Date of Patent: *Sep. 11, 2018

(54) STENTS WITH RADIOPAQUE MARKERS

(71) Applicant: Abbott Cardiovascular Systems Inc., Santa Clara, CA (US)

(72) Inventors: Stephen R. Dugan, San Francisco, CA (US); Anthony J. Abbate, Santa Clara, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/357,987

(22) Filed: Nov. 21, 2016

(65) Prior Publication Data

US 2017/0071764 A1    Mar. 16, 2017

Related U.S. Application Data

(63) Continuation of application No. 14/588,286, filed on Dec. 31, 2014, now Pat. No. 9,532,888, which is a continuation of application No. 11/325,973, filed on Jan. 4, 2006, now abandoned.

(51) Int. Cl.
| | |
|---|---|
| *A61F 2/91* | (2013.01) |
| *A61F 2/86* | (2013.01) |
| *A61F 2/915* | (2013.01) |
| *A61L 31/14* | (2006.01) |
| *A61L 31/18* | (2006.01) |

(Continued)

(52) U.S. Cl.
CPC .......... *A61F 2/86* (2013.01); *A61F 2/82* (2013.01); *A61F 2/91* (2013.01); *A61F 2/915* (2013.01); *A61L 31/148* (2013.01); *A61L 31/18* (2013.01); *A61B 90/39* (2016.02); *A61F 2002/91533* (2013.01); *A61F 2002/91558* (2013.01); *A61F 2002/91566* (2013.01); *A61F 2210/0004* (2013.01); *A61F 2250/0029* (2013.01); *A61F 2250/0036* (2013.01); *A61F 2250/0098* (2013.01)

(58) Field of Classification Search
CPC ...... A61F 2/91; A61F 2/07; A61F 2/82; A61F 2/86

See application file for complete search history.

(56) References Cited

U.S. PATENT DOCUMENTS

| | | |
|---|---|---|
| 2,697,863 A | 12/1954 | Moser |
| 3,476,463 A | 11/1969 | Kreuzer |
| 3,687,135 A | 8/1972 | Stroganov et al. |

(Continued)

FOREIGN PATENT DOCUMENTS

| | | |
|---|---|---|
| CN | 1241442 | 1/2000 |
| DE | 44 07 079 | 9/1994 |

(Continued)

OTHER PUBLICATIONS

International Search Report and Written Opinion dated Jun. 29, 2016, for International Application No. PCT/US2016/017333, 13 pages.

(Continued)

*Primary Examiner* — Jason-Dennis Stewart
(74) *Attorney, Agent, or Firm* — Squire Patton Boggs (US) LLP

(57) ABSTRACT

Various embodiments of stents with radiopaque markers disposed within depots in the stent, are described herein.

3 Claims, 7 Drawing Sheets

(51) Int. Cl.
*A61F 2/82* (2013.01)
*A61B 90/00* (2016.01)

(56) References Cited

U.S. PATENT DOCUMENTS

| | | | |
|---|---|---|---|
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,886,870 A | 12/1989 | D'Amore et al. |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,061,281 A | 10/1991 | Mares et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,380,976 A | 1/1995 | Couch |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,486,546 A | 1/1996 | Mathiesen et al. |
| 5,500,013 A | 3/1996 | Buscemi et al. |
| 5,502,158 A | 3/1996 | Sinclair et al. |
| 5,507,799 A | 4/1996 | Sumiya |
| 5,514,379 A | 5/1996 | Weissleder et al. |
| 5,525,646 A | 6/1996 | Lundgren et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,565,215 A | 10/1996 | Gref et al. |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,603,722 A | 2/1997 | Phan et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,656,186 A | 8/1997 | Mourou et al. |
| 5,667,767 A | 9/1997 | Greff et al. |
| 5,667,796 A | 9/1997 | Otten |
| 5,670,161 A | 9/1997 | Healy et al. |
| 5,670,558 A | 9/1997 | Onishi et al. |
| 5,686,540 A | 11/1997 | Kakizawa |
| 5,693,085 A | 12/1997 | Buirge et al. |
| 5,700,286 A | 12/1997 | Tartaglia et al. |
| 5,700,901 A | 12/1997 | Hurst et al. |
| 5,704,082 A | 1/1998 | Smith |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,725,572 A | 3/1998 | Lam et al. |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,327 A | 4/1998 | Frantzen |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,770,609 A | 6/1998 | Grainger et al. |
| 5,780,807 A | 7/1998 | Saunders |
| 5,800,516 A | 9/1998 | Fine et al. |
| 5,811,447 A | 9/1998 | Kunz et al. |
| 5,824,042 A | 10/1998 | Lombardi et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |

(56) References Cited

U.S. PATENT DOCUMENTS

| | | |
|---|---|---|
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,007,845 A | 12/1999 | Domb et al. |
| 6,010,445 A | 1/2000 | Armini et al. |
| 6,015,541 A | 1/2000 | Greff et al. |
| 6,022,374 A | 2/2000 | Imran |
| 6,042,606 A | 3/2000 | Frantzen |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,110,483 A | 8/2000 | Whitbourne et al. |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,131,266 A | 10/2000 | Saunders |
| 6,150,630 A | 11/2000 | Perry et al. |
| 6,153,252 A | 11/2000 | Hossainy et al. |
| 4,776,337 B1 | 12/2000 | Palmaz |
| 6,156,062 A | 12/2000 | McGuinness |
| 6,159,951 A | 12/2000 | Karpeisky et al. |
| 6,160,084 A | 12/2000 | Langer et al. |
| 6,160,240 A | 12/2000 | Momma et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,326 B1 | 1/2001 | Kitaoka et al. |
| 6,174,329 B1 | 1/2001 | Callol et al. |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,045 B1 | 2/2001 | Fehring et al. |
| 6,206,911 B1 | 3/2001 | Milo |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,254,632 B1 | 7/2001 | Wu et al. |
| 6,260,976 B1 | 7/2001 | Endou et al. |
| 6,273,913 B1 | 8/2001 | Wright et al. |
| 6,281,262 B1 | 8/2001 | Shikinami |
| 6,283,234 B1 | 9/2001 | Torbet |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,295,168 B1 | 9/2001 | Hofnagle et al. |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 6,334,871 B1 | 1/2002 | Dor et al. |
| 6,355,058 B1 | 3/2002 | Pacetti et al. |
| 6,361,557 B1 | 3/2002 | Gittings et al. |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,402,777 B1 | 6/2002 | Globerman et al. |
| 6,409,752 B1 | 6/2002 | Boatman et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,471,721 B1 | 10/2002 | Dang |
| 6,475,779 B2 | 11/2002 | Mathiowithz et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,506,437 B1 | 1/2003 | Harish et al. |
| 6,511,748 B1 | 1/2003 | Barrows |
| 6,517,888 B1 | 2/2003 | Weber |
| 6,521,865 B1 | 2/2003 | Jones et al. |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,563,080 B2 | 5/2003 | Shapovalov et al. |
| 6,563,998 B1 | 5/2003 | Farah et al. |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,582,472 B2 | 6/2003 | Hart |
| 6,585,755 B2 | 7/2003 | Jackson et al. |
| 6,585,765 B1 | 7/2003 | Hossainy et al. |

(56) References Cited

U.S. PATENT DOCUMENTS

| | | |
|---|---|---|
| 6,589,227 B2 | 7/2003 | Sonderskov |
| 6,592,614 B2 | 7/2003 | Lenker et al. |
| 6,592,617 B2 | 7/2003 | Thompson |
| 6,613,072 B2 | 9/2003 | Lau et al. |
| 6,620,194 B2 | 9/2003 | Ding et al. |
| 6,626,936 B2 | 9/2003 | Stinson |
| 6,626,939 B1 | 9/2003 | Burnside et al. |
| 6,635,269 B1 | 10/2003 | Jennissen |
| 6,641,607 B1 | 11/2003 | Hossainy et al. |
| 6,645,243 B2 | 11/2003 | Vallana et al. |
| 6,652,579 B1 | 11/2003 | Cox et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,722 B2 | 12/2003 | Chen et al. |
| 6,669,723 B2 | 12/2003 | Killion et al. |
| 6,676,697 B1 | 1/2004 | Richter |
| 6,679,980 B1 | 1/2004 | Andreacchi |
| 6,689,375 B1 | 2/2004 | Wahlig et al. |
| 6,695,920 B1 | 2/2004 | Pacetti et al. |
| 6,696,667 B1 | 2/2004 | Flanagan |
| 6,699,278 B2 | 3/2004 | Fischell et al. |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,505 B1 | 7/2004 | Hossainy et al. |
| 6,780,261 B2 | 8/2004 | Trozera |
| 6,801,368 B2 | 10/2004 | Coufal et al. |
| 6,805,898 B1 | 10/2004 | Wu et al. |
| 6,818,063 B1 | 11/2004 | Kerrigan |
| 6,822,186 B2 | 11/2004 | Strassl et al. |
| 6,846,323 B2 | 1/2005 | Yip et al. |
| 6,852,946 B2 | 2/2005 | Groen et al. |
| 6,858,680 B2 | 2/2005 | Gunatillake et al. |
| 6,863,685 B2 | 3/2005 | Davila et al. |
| 6,867,389 B2 | 3/2005 | Shapovalov et al. |
| 6,878,758 B2 | 4/2005 | Martin et al. |
| 6,891,126 B2 | 5/2005 | Matile |
| 6,899,729 B1 | 5/2005 | Cox et al. |
| 6,911,041 B1 | 6/2005 | Zscheeg |
| 6,913,762 B2 | 7/2005 | Caplice et al. |
| 6,918,928 B2 | 7/2005 | Wolinsky et al. |
| 6,926,733 B2 | 8/2005 | Stinson |
| 6,943,964 B1 | 9/2005 | Zhang et al. |
| 6,981,982 B2 | 1/2006 | Amstrong et al. |
| 6,981,987 B2 | 1/2006 | Huxel et al. |
| 7,022,132 B2 | 4/2006 | Kocur |
| 7,128,737 B1 | 10/2006 | Goder et al. |
| 7,163,555 B2 | 1/2007 | Dinh |
| 7,166,099 B2 | 1/2007 | Devens, Jr. |
| 7,226,475 B2 | 6/2007 | Lenz et al. |
| 7,243,408 B2 | 7/2007 | Vietmeier |
| 7,326,245 B2 | 2/2008 | Rosenthal et al. |
| 7,331,986 B2 | 2/2008 | Brown et al. |
| 7,500,988 B1 | 3/2009 | Butaric et al. |
| 7,776,926 B1 | 8/2010 | Hossainy et al. |
| 8,002,817 B2 | 8/2011 | Limon |
| 8,303,644 B2 | 11/2012 | Lord et al. |
| 8,388,673 B2 | 3/2013 | Yang et al. |
| 8,539,663 B2 | 9/2013 | Wang et al. |
| 8,752,268 B2 | 6/2014 | Wu |
| 9,345,597 B2 | 5/2016 | Pachetti |
| 2001/0001317 A1 | 5/2001 | Duerig et al. |
| 2001/0010003 A1 | 7/2001 | Lai |
| 2001/0021871 A1 | 9/2001 | Stinson |
| 2001/0021873 A1 | 9/2001 | Stinson |
| 2001/0027339 A1 | 10/2001 | Boatman et al. |
| 2001/0029398 A1 | 10/2001 | Jadhav |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0032486 A1 | 3/2002 | Lazarovitz et al. |
| 2002/0062148 A1 | 5/2002 | Hart |
| 2002/0065553 A1 | 5/2002 | Weber |
| 2002/0111590 A1 | 8/2002 | Davila et al. |
| 2002/0116050 A1 | 8/2002 | Kocur |
| 2002/0138133 A1 | 9/2002 | Lenz et al. |
| 2002/0143386 A1 | 10/2002 | Davila et al. |
| 2002/0161114 A1 | 10/2002 | Gunatillake et al. |
| 2002/0190038 A1 | 12/2002 | Lawson |
| 2002/0193862 A1 | 12/2002 | Mitelberg et al. |
| 2003/0004563 A1 | 1/2003 | Jackson et al. |
| 2003/0009235 A1 | 1/2003 | Manrique et al. |
| 2003/0028241 A1 | 2/2003 | Stinson |
| 2003/0028245 A1 | 2/2003 | Barclay et al. |
| 2003/0033001 A1 | 2/2003 | Igaki |
| 2003/0039689 A1 | 2/2003 | Chen et al. |
| 2003/0050688 A1 | 3/2003 | Fischell et al. |
| 2003/0060872 A1 | 3/2003 | Gomringer et al. |
| 2003/0065355 A1 | 4/2003 | Weber |
| 2003/0069630 A1 | 4/2003 | Burgermeister et al. |
| 2003/0093107 A1 | 5/2003 | Parsonage et al. |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0108588 A1 | 6/2003 | Chen |
| 2003/0121148 A1 | 7/2003 | DiCaprio |
| 2003/0153971 A1 | 8/2003 | Chandrasekaran |
| 2003/0155328 A1 | 8/2003 | Huth et al. |
| 2003/0171053 A1 | 9/2003 | Sanders |
| 2003/0187495 A1 | 10/2003 | Cully et al. |
| 2003/0204245 A1 | 10/2003 | Brightbill |
| 2003/0208259 A1 | 11/2003 | Penhasi |
| 2003/0209835 A1 | 11/2003 | Chun et al. |
| 2003/0226833 A1 | 12/2003 | Shapovalov et al. |
| 2003/0236563 A1 | 12/2003 | Fifer |
| 2004/0015228 A1 | 1/2004 | Lombardi et al. |
| 2004/0024449 A1 | 2/2004 | Boyle |
| 2004/0027339 A1 | 2/2004 | Schulz |
| 2004/0044399 A1 | 3/2004 | Ventura |
| 2004/0073291 A1 | 4/2004 | Brown et al. |
| 2004/0078071 A1 | 4/2004 | Escamilla et al. |
| 2004/0088039 A1 | 5/2004 | Lee et al. |
| 2004/0093077 A1 | 5/2004 | White et al. |
| 2004/0098090 A1 | 5/2004 | Williams et al. |
| 2004/0098095 A1 | 5/2004 | Burnside et al. |
| 2004/0102758 A1 | 5/2004 | Davila et al. |
| 2004/0106987 A1 | 6/2004 | Palasis et al. |
| 2004/0111149 A1 | 6/2004 | Stinson |
| 2004/0122509 A1 | 6/2004 | Brodeur |
| 2004/0126405 A1 | 7/2004 | Sahatjian |
| 2004/0127970 A1 | 7/2004 | Saunders et al. |
| 2004/0143180 A1 | 7/2004 | Zhong et al. |
| 2004/0143317 A1 | 7/2004 | Stinson et al. |
| 2004/0167610 A1 | 8/2004 | Fleming, III |
| 2004/0167619 A1 | 8/2004 | Case et al. |
| 2004/0181236 A1 | 9/2004 | Eidenschink et al. |
| 2004/0204750 A1 | 10/2004 | Dinh |
| 2004/0220662 A1 | 11/2004 | Dang et al. |
| 2004/0236428 A1 | 11/2004 | Burkinshaw et al. |
| 2005/0004653 A1 | 1/2005 | Gerberding et al. |
| 2005/0004663 A1 | 1/2005 | Llanos et al. |
| 2005/0015138 A1 | 1/2005 | Schuessler et al. |
| 2005/0021131 A1 | 1/2005 | Venkatraman et al. |
| 2005/0060025 A1 | 3/2005 | Mackiewicz et al. |
| 2005/0087520 A1 | 4/2005 | Wang et al. |
| 2005/0107865 A1 | 5/2005 | Clifford et al. |
| 2005/0111500 A1 | 5/2005 | Harter et al. |
| 2005/0147647 A1 | 7/2005 | Glauser et al. |
| 2005/0154450 A1 | 7/2005 | Larson et al. |
| 2005/0157382 A1 | 7/2005 | Kafka et al. |
| 2005/0172471 A1 | 8/2005 | Vietmeier |
| 2005/0211680 A1 | 9/2005 | Li et al. |
| 2005/0222673 A1 | 10/2005 | Nicholas |
| 2005/0283226 A1 | 12/2005 | Haverkost |
| 2005/0283228 A1 | 12/2005 | Stanford |
| 2006/0025847 A1 | 2/2006 | Parker |

(56) References Cited

U.S. PATENT DOCUMENTS

| | | |
|---|---|---|
| 2006/0033240 A1 | 2/2006 | Weber et al. |
| 2006/0120418 A1 | 6/2006 | Harter et al. |
| 2006/0173528 A1 | 8/2006 | Feld et al. |
| 2006/0195175 A1 | 8/2006 | Bregulla |
| 2006/0204556 A1 | 9/2006 | Daniels et al. |
| 2006/0241741 A1 | 10/2006 | Lootz |
| 2007/0021834 A1 | 1/2007 | Young et al. |
| 2007/0038290 A1 | 2/2007 | Huang et al. |
| 2007/0156230 A1 | 7/2007 | Dugan et al. |
| 2007/0179610 A1 | 8/2007 | Biedermann et al. |
| 2007/0195006 A1 | 8/2007 | Frye et al. |
| 2007/0266542 A1 | 11/2007 | Melsheimer |
| 2007/0276476 A1 | 11/2007 | Llanos et al. |
| 2007/0293938 A1 | 12/2007 | Gale et al. |
| 2008/0009938 A1 | 1/2008 | Huang et al. |
| 2008/0015684 A1 | 1/2008 | Wu |
| 2008/0033532 A1 | 2/2008 | Dave |
| 2008/0051868 A1 | 2/2008 | Cottone et al. |
| 2008/0051873 A1 | 2/2008 | Cottone et al. |
| 2008/0188924 A1 | 8/2008 | Prabhu |
| 2008/0243226 A1 | 10/2008 | Fernandez et al. |
| 2009/0076594 A1 | 3/2009 | Sabaria |
| 2009/0105761 A1 | 4/2009 | Robie |
| 2009/0112207 A1 | 4/2009 | Walker et al. |
| 2009/0204203 A1 | 8/2009 | Allen et al. |
| 2010/0004735 A1 | 1/2010 | Yang et al. |
| 2010/0042215 A1 | 2/2010 | Stalcup et al. |
| 2010/0094405 A1 | 4/2010 | Cottone |
| 2011/0130521 A1 | 6/2011 | Thatcher et al. |
| 2011/0138022 A1 | 6/2011 | Xie et al. |
| 2011/0208190 A1 | 8/2011 | Kumbar et al. |
| 2011/0238156 A1 | 9/2011 | Tischler et al. |
| 2011/0282428 A1 | 11/2011 | Meyer et al. |
| 2012/0042501 A1 | 2/2012 | Wang et al. |
| 2012/0082919 A1 | 4/2012 | Fircho et al. |
| 2012/0271361 A1 | 10/2012 | Zhou et al. |
| 2013/0131780 A1 | 5/2013 | Armstrong et al. |
| 2013/0150943 A1 | 6/2013 | Zheng et al. |
| 2013/0255853 A1 | 10/2013 | Wang et al. |
| 2013/0325104 A1 | 12/2013 | Wu |
| 2013/0325105 A1 | 12/2013 | Wu |
| 2013/0325107 A1 | 12/2013 | Wu |
| 2013/0331926 A1 | 12/2013 | Wu |
| 2014/0369435 A1 | 12/2014 | Kneckt et al. |
| 2016/0120671 A1 | 5/2016 | Higashi et al. |
| 2016/0228267 A1 | 8/2016 | Pacetti et al. |
| 2016/0242851 A1 | 8/2016 | Lumauig |
| 2016/0361182 A1 | 12/2016 | Lumauig et al. |

FOREIGN PATENT DOCUMENTS

| | | |
|---|---|---|
| DE | 197 31 021 | 1/1999 |
| DE | 198 56 983 | 12/1999 |
| DE | 297 24 852 | 2/2005 |
| DE | 103 61 942 | 7/2005 |
| DE | 10 2004 04599 | 3/2006 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 583 170 | 2/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 714 641 | 6/1996 |
| EP | 0 842 729 | 5/1998 |
| EP | 0 970 711 | 1/2000 |
| EP | 1 210 922 | 6/2002 |
| EP | 1 277 449 | 1/2003 |
| EP | 1 479 358 | 11/2004 |
| EP | 1 570 808 | 9/2005 |
| EP | 1 591 079 | 11/2005 |
| EP | 1 656 905 | 5/2006 |
| EP | 2 438 891 A1 | 4/2012 |
| EP | 2 752 173 A1 | 7/2014 |
| GB | 2 247 696 | 3/1992 |
| JP | 04-033791 | 2/1992 |
| JP | 07-124766 | 5/1995 |
| JP | 10-166156 | 6/1998 |
| JP | 2002-233578 | 8/2002 |
| JP | 2003-053577 | 2/2003 |
| JP | 2004-358242 | 12/2004 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/27587 | 10/1995 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/20429 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 02/26162 | 4/2002 |
| WO | WO 02/38325 | 5/2002 |
| WO | WO 03/015664 | 2/2003 |
| WO | WO 03/015978 | 2/2003 |
| WO | WO 03/047463 | 6/2003 |
| WO | WO 03/057075 | 7/2003 |
| WO | WO 2004/019820 | 3/2004 |
| WO | WO 2004/023985 | 3/2004 |
| WO | WO 2004/062533 | 7/2004 |
| WO | WO 2004/112863 | 12/2004 |
| WO | WO 2005/023480 | 3/2005 |
| WO | WO 2007/081551 | 7/2007 |
| WO | WO 2014/064180 | 5/2014 |
| WO | WO 2014/181713 | 11/2014 |

OTHER PUBLICATIONS

Acquarulo et al., *Enhancing Medical Device Performance with Nanocomposite Poly*, Med. Device Link, www.devicelink.com/grabber.php3?URL downloaded Mar. 26, 2007, 4 pgs.

Anonymous, *Bioabsorbable stent mounted on a catheter having optical coherence tomography capabilities*, Research Disclosure, Sep. 2004, pp. 1159-1162.

Ansari, *End-to-end tubal anastomosis using an absorbable stent*, Fertility and Sterility, vol. 32(2), pp. 197-201 (Aug. 1979).

Ansari, *Tubal Reanastomosis Using Absorbable Stent*, International Journal of Fertility, vol. 23(4), pp. 242-243 (1978).

Bull, *Parylene Coating for Medical Applications*, Medical Product Manufacturing News 18, 1 pg. (Mar. 1993).

Casper et al., *Fiber-Reinforced Absorbable Composite for Orthopedic Surgery*, Polymeric Materials Science and Engineering, vol. 53 pp. 497-501 (1985).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar. /Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

(56) References Cited

OTHER PUBLICATIONS

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).
Devanathan et al., *Polymeric Conformal Coatings for Implantable Electronic Devices*, IEEE Transactions on Biomedical Engineering, vol. BME-27(11), pp. 671-675 (1980).
Eidelman et al., *Characterization of Combinatorial Polymer Blend Composition Gradients by FTIR Microspectroscopy*, J. Res. Natl. Inst. Standards and Technol., vol. 109, No. 2, pp. 219-231 (2004).
Elbert et al., *Conjugate Addition Reactions Combined with Free-Radical Cross-Linking for the Design of Materials for Tissue Engineering*, Biomacromolecules, vol. 2, pp. 430-441 (2001).
Fan et al., *Plasma Absorption of Femtosecond Laser Pulses in Dielectrics*, J. of Heat Transfer, vol. 124, pp. 275-283 (2002).
Hahn et al., *Biocompatibility of Glow-Discharge-Polymerized Films and Vacuum-Deposited Parylene*, J Applied Polymer Sci, vol. 38, pp. 55-64 (1984).
Hahn et al., *Glow Discharge Polymers as Coatings for Implanted Devices*, ISA, pp. 109-111 (1981).
He et al., *Assessment of Tissue Blood Flow Following Small Artery Welding with an Intraluminal Dissolvable Stent*, Microsurgery, vol. 19(3), pp. 148-152 (1999).
Hoffnagle et al., *Design and performance of a refractive optical system that converts a Gaussian to a flattop beam*, Applied Optics, vol. 39, No. 30 pp. 5488-5499 (2000).
Kelley et al., *Totally Resorbable High-Strength Composite Material*, Advances in Biomedical Polymers, vol. 35, pp. 75-85 (1987).
Kubies et al., *Microdomain Structure in polylactide-block-poly(ethylene oxide) copolymer films*, Biomaterials, vol. 21, pp. 529-536 (2000).
Kutryk et al., *Coronary Stenting: Current Perspectives*, a companion to the Handbook of Coronary Stents, pp. 1-16 (1999).
Martin et al., *Enhancing the biological activity of immobilized osteopontin using a type-1 collagen affinity coating*, J. Biomed. Mater. Res., vol. 70A, pp. 10-19 (2004).
Mauduit et al., *Hydrolytic degradation of films prepared from blends of high and low molecular weight poly(DL-lactic acid)s*, J. Biomed. Mater. Res., vol. 30, pp. 201-207 (1996).
Middleton et al., *Synthetic biodegradable polymers as orthopedic devices*, Biomaterials, vol. 21, pp. 2335-2346 (2000).
Muller et al., *Advances in Coronary Angioplasty: Endovascular Stents*, Coron. Arter. Dis., vol. 1(4), pp. 438-448 (Jul./Aug. 1990).
Nichols et al., *Electrical Insulation of Implantable Devices by Composite Polymer Coatings*, ISA Transactions, vol. 26(4), pp. 15-18 (1987).
Peuster et al., *A novel approach to temporary stenting: degradable cardiovascular stents produced from corrodible metal-results 6-18 months after implantation into New Zealand white rabbits*, Heart, vol. 86, pp. 563-569 (2001).
Pietrzak et al., *Bioabsorbable Fixation Devices: Status for the Craniomaxillofacial Surgeon*, J. Craniofaxial Surg., vol. 2, pp. 92-96 (1997).
Pietrzak et al., *Bioresorbable implants—practical considerations*, Bone, vol. 19, No. 1, Supplement Jul. 1996, pp. 109S-119S.
Redman, *Clinical Experience with Vasovasostomy Utilizing Absorbable Intravasal Stent*, Urology, vol. 20(1), pp. 59-61 (Jul. 1982).
Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).
Schatz, *A View of Vascular Stents*, Circulation, vol. 79(2), pp. 445-457 (Feb. 1989).
Schmidt et al., *Long-Term Implants of Parylene-C Coated Microelectrodes*, Med & Biol Eng & Comp, vol. 26(1), pp. 96-101 (Jan. 1988).
Spagnuolo et al., *Gas 1 is induced by VE-cadherin and vascular endothelial growth factor and inhibits endothelial cell apoptosis*, Blood, vol. 103, pp. 3005-3012 (2004).
Sun et al., *Inert gas beam delivery for ultrafast laser micromachining at ambient pressure*, Am. Inst. Of Physics, 6 pgs.
Tamai et al., *Initial and 6-Month Results of Biodegradable Poly-I-Lactic Acid Coronary Stents in Humans*, Circulation, pp. 399-404 (Jul. 25, 2000).
Tsuji et al., *Biodegradable Polymeric Stents*, Current Interventional Cardiology Reports, vol. 3, pp. 10-17 (2001).
Völkel et al., *Targeting of immunoliposomes to endothelial cells using a single-chain Fv fragment directed against human endoglin (CD105)*, Biochimica et Biophysica Acta 1663, pp. 158-166 (2004).
Von Recum et al., *Degradation of polydispersed poly(L-lactic acid) to modulate lactic acid release*, Biomaterials, vol. 16, pp. 441-445 (1995).
Yau et al., *Modern Size-Exclusion Liquid Chromatography*, Wiley-Interscience Publication, IX-XV (1979).
Zhang et al., *Single-element laser beam shaper for uniform flat-top profiles*, Optics Express, vol. 11, No. 16, pp. 1942-1948 (2003).
International Search Report and Written Opinion dated Jun. 15, 2007 in International Patent Application No. PCT/US2006/049269, 19 pages.
International Search Report and Written Opinion dated Dec. 4, 2007 in International Patent Application No. PCT/US2007/015561, 10 pages.
Office Action dated Mar. 31, 2011 in European Patent Application No. 06848153.0, 4 pages.
Office Action dated Aug. 16, 2011 in Japanese Patent Application No. P2008-549504, 6 pages.
Office Action dated Mar. 27, 2012 in Japanese Patent Application No. P2008-549504, 6 pages.
Extended European Search Report dated Jun. 3, 2014 in European Patent Application No. 13161281.4, 9 pages.
Office Action dated Jun. 22, 2015 in European Patent Application No. 14200352.4, 7 pages.
Extended European Search Report dated Jan. 31, 2017 in European Patent Application No. 16177926.9, 7 pages.

STENTS WITH RADIOPAQUE MARKERS

CROSS REFERENCE

This application is a continuation of application Ser. No. 11/325,973, filed on Jan. 4, 2006. Application Ser. No. 11/325,973 is incorporated herein by reference it its entirety, including all of the figures.

BACKGROUND OF THE INVENTION

Field of the Invention

This invention relates to implantable medical devices, such as stents. In particular, the invention relates to polymeric stents with radiopaque markers.

Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The structure of stents is typically composed of scaffolding that includes a pattern or network of interconnecting structural elements or struts. The scaffolding can be formed from wires, tubes, or sheets of material rolled into a cylindrical shape. In addition, a medicated stent may be fabricated by coating the surface of either a metallic or polymeric scaffolding with a polymeric carrier. The polymeric scaffolding may also serve as a carrier of an active agent or drug.

The first step in treatment of a diseased site with a stent is locating a region that may require treatment such as a suspected lesion in a vessel, typically by obtaining an x-ray image of the vessel. To obtain an image, a contrast agent, which contains a radiopaque substance such as iodine is injected into a vessel. "Radiopaque" refers to the ability of a substance to absorb x-rays. The x-ray image depicts the lumen of the vessel from which a physician can identify a potential treatment region. The treatment then involves both delivery and deployment of the stent. "Delivery" refers to introducing and transporting the stent through a bodily lumen to a region in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn allowing the stent to self-expand.

The stent must be able to simultaneously satisfy a number of mechanical requirements. First, the stent must be capable of withstanding the structural loads, namely radial compressive forces, imposed on the stent as it supports the walls of a vessel lumen. In addition to having adequate radial strength or more accurately, hoop strength, the stent should be longitudinally flexible to allow it to be maneuvered through a tortuous vascular path and to enable it to conform to a deployment site that may not be linear or may be subject to flexure. The material from which the stent is constructed must allow the stent to undergo expansion, which typically requires substantial deformation of localized portions of the stent's structure. Once expanded, the stent must maintain its size and shape throughout its service life despite the various forces that may come to bear thereon, including the cyclic loading induced by the beating heart. Finally, the stent must be biocompatible so as not to trigger any adverse vascular responses.

In addition to meeting the mechanical requirements described above, it is desirable for a stent to be radiopaque, or fluoroscopically visible under x-rays. Accurate stent placement is facilitated by real time visualization of the delivery of a stent. A cardiologist or interventional radiologist can track the delivery catheter through the patient's vasculature and precisely place the stent at the site of a lesion. This is typically accomplished by fluoroscopy or similar x-ray visualization procedures. For a stent to be fluoroscopically visible it must be more absorptive of x-rays than the surrounding tissue. Radiopaque materials in a stem may allow for its direct visualization.

In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials may be configured to meet this additional clinical requirement since they may be designed to completely erode after the clinical need for them has ended. Stents fabricated from biodegradable polymers are particularly promising, in part because they may be designed to completely erode within a desired time frame.

However, a significant shortcoming of biodegradable polymers (and polymers generally composed of carbon, hydrogen, oxygen, and nitrogen) is that they are radiolucent with no radiopacity. Biodegradable polymers tend to have x-ray absorption similar to body tissue.

One way of addressing this problem is to attach radiopaque markers to structural elements of the stent. A radiopaque marker can be disposed within a structural element in such a way that the marker is secured to the structural element. However, the use of stent markers on polymeric stents entails a number of challenges. One challenge relates to the difficulty of insertion of markers.

Another challenge pertains to the fact that some regions of polymeric struts tend to undergo significant deformation or strain during crimping and expansion. In particular, such changes are due to plastic deformation of polymers. Thus, during stent deployment, the portion of a stent containing an element may crack or stretch as stress is being applied to the expanding stent. As a result, the marker may become dislodged.

SUMMARY OF THE INVENTION

Embodiments of the present invention are directed to a stent including a deformed radiopaque marker disposed in a depot in a portion of the stent. The marker may be coupled to the portion at least partially by an interference fit between an expanded portion of the marker and an internal surface of the portion of the stent within the depot. In an embodiment, at least some gaps between the deformed marker and the internal surface may be filled with a polymeric coating material. The markers may include sufficient radiopacity to be imaged by an imaging technique.

Further embodiments of the present invention are directed to a method of fabricating a stent that may include disposing a radiopaque marker in a depot in a portion of the stent and compressing the marker to couple the marker within the depot. In an embodiment, compressing the marker may expand a portion of the marker within the depot to create an interference fit between the expanded portion and an internal surface of the stent within the depot. The method may further include applying a coating material to fill gaps between the deformed marker and the internal surface.

Other embodiments of the present invention are directed to a stent including a radiopaque marker disposed in a depot in a portion of the stent such that the marker may be coupled to the stent at least partially by an interference fit between the marker and a deformed portion of the stent adjacent to the depot.

Additional embodiments of the present invention are directed to a stent including a radiopaque marker disposed in a depot in a portion of the stent that is configured to accommodate the marker such that a surface of the portion adjacent to the depot may include a recess. The recess may facilitate deformation of the portion when the marker is disposed within the depot so as to facilitate coupling of the marker to the portion.

Additional embodiments of the present invention are directed to a stent including a marker disposed within a depot in a portion of the stent such that the stent may have regions with a lower strain than other higher strain portions when the stent is placed under an applied stress during use. The depot may be selectively positioned in a selected region of lower strain.

DETAILED DESCRIPTION OF THE INVENTION

The present invention may be applied to stents and, more generally, implantable medical devices such as, but is not limited to, self-expandable stents, balloon-expandable stents, stent-grafts, vascular grafts, cerebrospinal fluid shunts, pacemaker leads, closure devices for patent foramen ovale, and synthetic heart valves.

A stent can have virtually any structural pattern that is compatible with a bodily lumen in which it is implanted. Typically, a stent is composed of a pattern or network of circumferential and longitudinally extending interconnecting structural elements or struts. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility. The present invention is applicable to virtually any stent design and is, therefore, not limited to any particular stent design or pattern. One embodiment of a stent pattern may include cylindrical rings composed of struts. The cylindrical rings may be connected by connecting struts.

In some embodiments, a stent of the present invention may be formed from a tube by laser cutting the pattern of struts in the tube. The stent may also be formed by laser cutting a polymeric sheet, rolling the pattern into the shape of the cylindrical stent, and providing a longitudinal weld to form the stent. Other methods of forming stents are well known and include chemically etching a polymeric sheet and rolling and then welding it to form the stent. A polymeric wire may also be coiled to form the stent. The stent may be formed by injection molding of a thermoplastic or reaction injection molding of a thermoset polymeric material. Filaments of the compounded polymer may be extruded or melt spun. These filaments can then be cut, formed into ring elements, welded closed, corrugated to form crowns, and then the crowns welded together by heat or solvent to form the stent. Lastly, hoops or rings may be cut from tubing stock, the tube elements stamped to form crowns, and the crowns connected by welding or laser fusion to form the stent.

Figure 1:
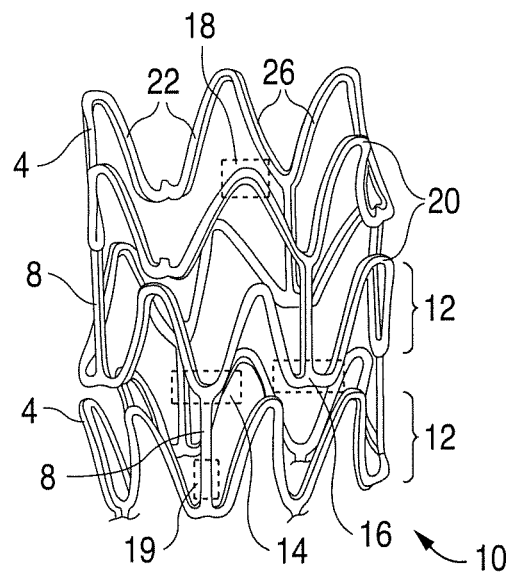
FIG. 1 depicts a three-dimensional view of a cylindrically-shaped stent.

FIG. 1 depicts a three-dimensional view of a cylindrically-shaped stent 10 with struts 4 that form cylindrical rings 12 which are connected by linking struts 8. The cross-section of the struts in stent 10 is rectangular-shaped. The struts have abluminal faces 20, luminal faces 22, and sidewall faces 26. The cross-section of struts is not limited to what has been illustrated, and therefore, other cross-sectional shapes are applicable with embodiments of the present invention. The pattern should not be limited to what has been illustrated as other stent patterns are easily applicable with embodiments of the present invention.

A stent can be made of a biostable and/or biodegradable polymer. As indicated above, a stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind. The duration can be in a range from about a month to a few years. However, the duration is typically in a range from about one month to twelve months, or in some embodiments, six to twelve months. It is important for the stent to provide mechanical support to a vessel for at least a portion of the duration. Many biodegradable polymers have erosion rates that make them suitable for treatments that require the presence of a device in a vessel for the above-mentioned time-frames.

In general, polymers can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and can be gradually resorbed, absorbed and/or eliminated by the body.

Biodegradation refers generally to changes in physical and chemical properties that occur in a polymer upon exposure to bodily fluids as in a vascular environment. The changes in properties may include a decrease in molecular weight, deterioration of mechanical properties, and decrease in mass due to erosion or absorption. Mechanical properties may correspond to strength and modulus of the polymer. Deterioration of the mechanical properties of the polymer decreases the ability of a stent, for example, to provide mechanical support in a vessel. The decrease in molecular weight may be caused by, for example, hydrolysis, oxidation, enzymolysis, and/or metabolic processes.

Representative examples of polymers that may be used to fabricate embodiments of stents, or more generally, implantable medical devices include, but are not limited to, poly (N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D, L-lactide), poly(L-lactide-co-D,L-lactide), poly(caprolactone), poly(L-lactide-co-caprolactone), poly(D,L-lactide-co-caprolactone), poly(glycolide-co-caprolactone), poly (trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol.

It is generally desirable to minimize the interference of a stent or marker with the structure of a lumen and/or with flow of bodily fluid through the lumen. Sharp edges, protrusions, etc. in the path of blood flow can result in formation of turbulent and stagnant zones which can act as a nidus for thrombosis. A smaller and/or smoother profile of a body portion may be more hemocompatible. Additionally, a smaller and smoother profile presented by a marker has much less likelihood of catching on other parts of the delivery system such as the guidewire or guiding catheter. The embodiments of stents with markers discussed herein do not contribute significantly to the form factor, or profile, of the stent in such a way that interferes with the structure of a lumen and/or with flow of bodily fluid through the lumen.

As indicated above, it is desirable to have the capability of obtaining images of polymeric stents with x-ray fluoroscopy during and after implantation. Various embodiments of the present invention include stents with markers disposed within depots or holes in a stent. In an embodiment, the depot may be formed in a structural element by laser machining. The depot may extend partially or completely through the portion of the stent. For example, an opening of a depot may be on an abluminal or luminal surface and extend partially through the stent or completely through to an opposing surface. The markers may be sufficiently radiopaque for imaging the stent. In addition, embodiments of the stents with markers tend to be biocompatible and do not interfere with treatment.

Figure 2:
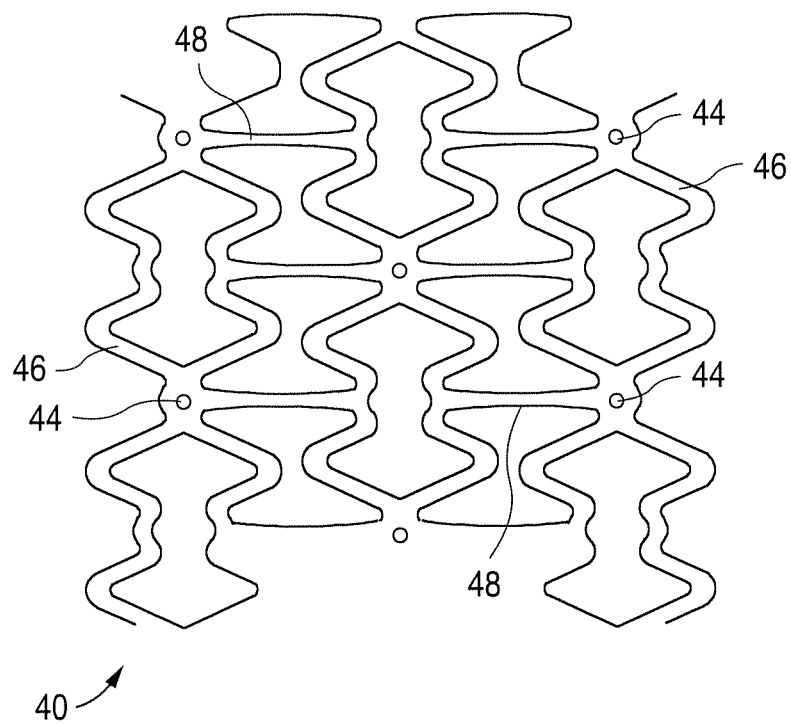
FIG. 2 depicts one embodiment of a stent pattern with a depot for receiving a marker.

FIG. 2 depicts one embodiment of a stent pattern 40 with depots 44 for receiving a marker. In FIG. 2, stent pattern 40 is shown in a flattened condition showing an abluminal or luminal surface so that the pattern can be clearly viewed. When the flattened portion of stent pattern 40 is in a cylindrical condition, it forms a radially expandable stent. Stent pattern 40 includes cylindrically aligned structural elements 46 and linking structural elements 48. Depots 44 are located at a region of intersection of six structural elements or a "spider" region.

Figure 3:
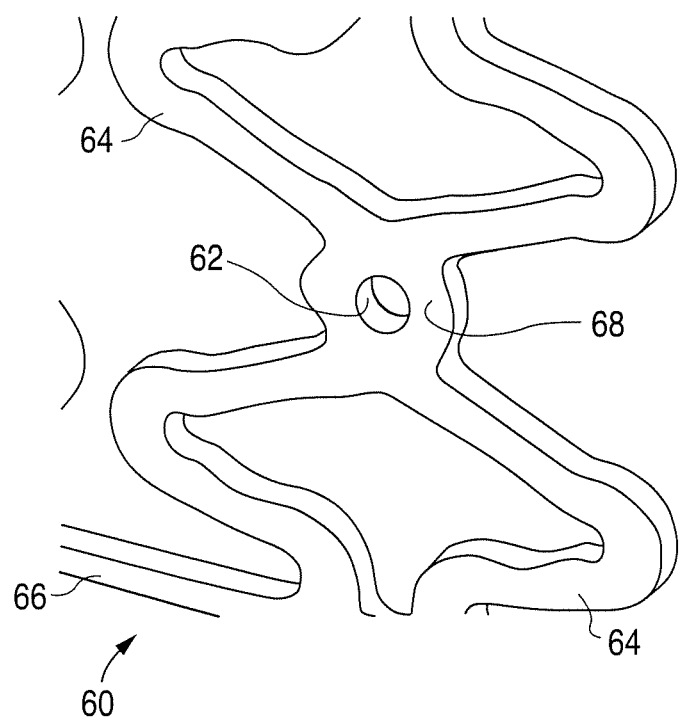
FIG. 3 depicts view of a stent pattern with a marker depot.

FIG. 3 depicts a three-dimensional view of a stent pattern 60 with depots 62. Stent pattern 60 includes cylindrically aligned structural elements 64 and linking structural elements 66. Depots 62 are located in a portion 68 which is a region of intersection of four structural elements. As depicted in FIG. 3, depots 62 have a cylindrical shape and extend completely through the radial thickness of structural elements in portion 68.

Figure 4A:
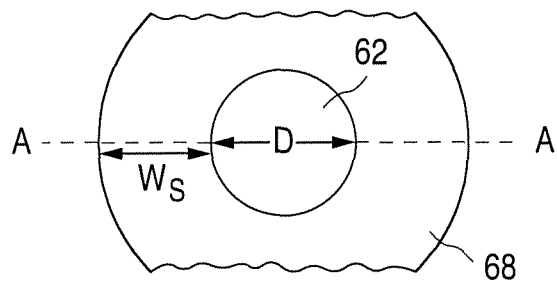
FIGS. 4A-B depict an overhead and side view of the portion of the stent from FIG. 3 with the marker depot.
Figure 4B:
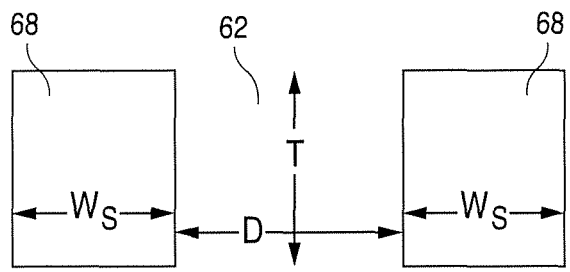

FIG. 4A depicts an overhead view of depot 62 in portion 68 from FIG. 3. FIG. 4B is a side view of depot 62 in portion 68 across line A-A in FIG. 4A. Depot 62 has a diameter D and extends all the way through portion 68 which has a radial thickness T. Portion 68 has a width $W_S$ along line A-A. D may be greater than 60%, 80%, 100%, 110%, 120%, 130%, or 140% of $W_S$.

Certain embodiments of a stent may include a deformed radiopaque marker disposed in a depot in a portion of the stent. The marker may be coupled to the portion at least partially by an interference fit between an expanded section of the marker and an internal surface of the portion of the stent within the depot. In some embodiments, a marker in an undeformed state may be disposed in a depot and compressed to couple the marker within the depot. Compressing the marker may expand a portion of the marker within the depot to create the interference fit. After compressing, the deformed marker may have at least one compressed portion in addition to the expanded portion.

There may be difficulties with the insertion of markers of certain shapes in the depots. For example, it may be necessary to orient or align a cylindrical element for insertion into a cylindrical depot. Cylindrical markers or slugs can be difficult to insert due to rotation of the slug during insertion.

Figure 5:
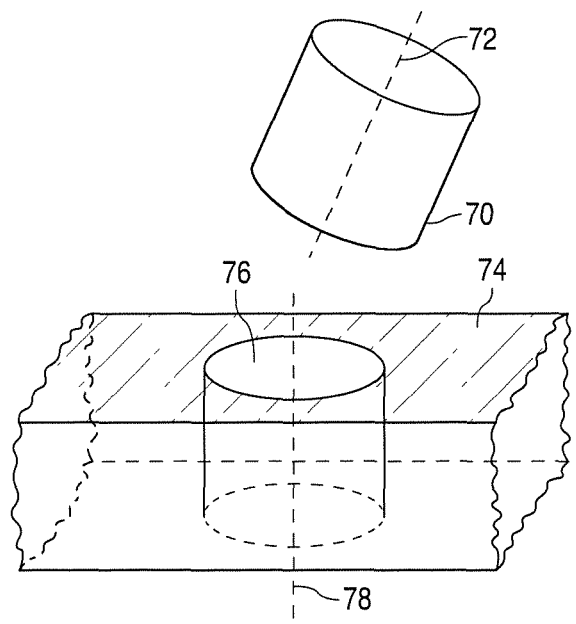
FIG. 5 depicts a cylindrical marker and a portion of a stent with a marker depot.

FIG. 5 depicts an example of a cylindrical marker 70 having a cylindrical axis 72. Also shown is a portion 74 of a stent with a cylindrical depot 76 having a cylindrical axis 78. During insertion, cylindrical marker 70 can rotate so that its axis 72 is not in alignment with axis 78 of depot 76.

Figure 6:
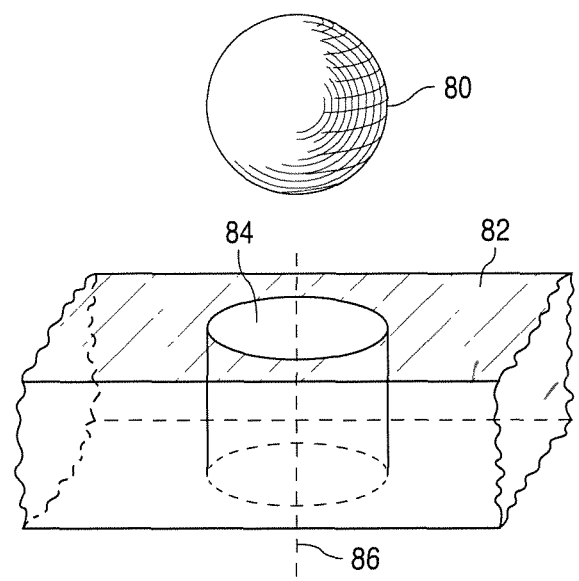
FIG. 6 depicts a spherical marker and a portion of a stent with a marker depot.

However, it is not necessary to orient a spherical marker due to the spherical symmetry of the marker. A spherical marker can be selected that has a size that allows the marker to fit into a depot. FIG. 6 depicts a spherical marker 80 and a portion 82 of a stent with a cylindrical depot 84 with an axis 86.

Figure 7:
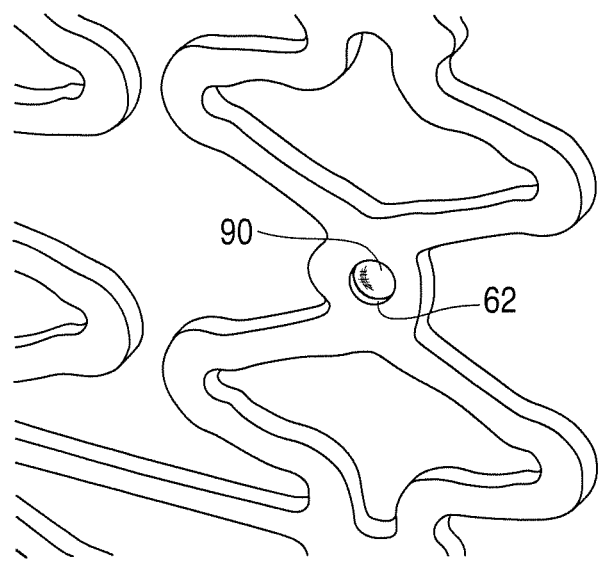
FIG. 7 depicts a spherical marker disposed within a depot in a stent.

FIG. 7 depicts the stent pattern of FIG. 3 with a spherical marker 90 disposed within depot 62. In some embodiments, the spherical marker may be completely enclosed within the depot. In other embodiments, the marker may partially project beyond a surface of the stent.

In some embodiments, a marker disposed in a depot may be compressed at the portions at the openings of the depot. The marker may then expand within the depot to create an interference fit. The compressed portion may correspond to compressed ends with an expanded portion between the ends. An interference fit may be between the expanded portion of the marker and the internal surface of the depot. For example, a spherical marker may be compressed at two ends and expand about an equator. In an embodiment, the marker may have a size that allows an interference fit within the depot. Such an interference fit may be particularly useful for markers composed of materials that are relatively easily deformed or malleable, such as, but not limited to gold.

In one embodiment, a marker may be placed in the depot and then pressed into place with a small flat tool or a machined fixture. In an embodiment, the marker may be disposed in a depot using a syringe. The markers may be held at the end of the syringe by a vacuum or surface tension of a viscous fluid. In some embodiments, the markers may be heated prior to placement into the depot.

After disposing and compressing the marker, there may be gaps between the marker and the internal surface of the depot. Such gaps may allow a marker to become loose and fall out of the depot. In some embodiments, at least some of the gaps between the deformed marker and the internal surface may be filled with a polymeric coating. A coating material composed of a polymer dissolved in a solvent may be applied to fill the gaps. The coating material may be applied in various ways known in the art such as by spraying or dipping.

Figure 8A:
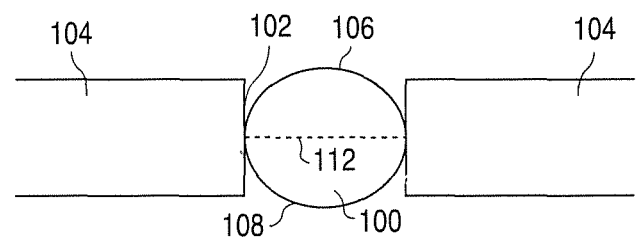
FIG. 8A depicts a side view of an uncompressed spherical marker in a depot.
Figure 8B:
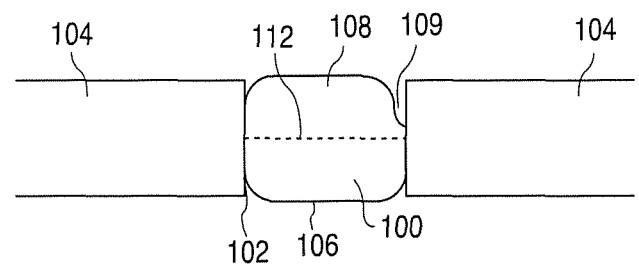
FIG. 8B depicts a side view of a compressed spherical marker in a depot.

FIG. 8A depicts a side view, as in FIG. 4B, across a portion 104 of a stent with a depot 102 with a spherical marker 100 disposed within depot 102. FIG. 8B illustrates an interference fit between marker 100 and portion 104. Marker 100 is compressed at ends 106 and 108 which causes expansion around an equator 112. A void 109 may be filled with a polymeric coating material, as described above.

Some materials that are desirable for use in markers such as platinum may be difficult to compress and deform to create an interference fit. Compressing such materials may cause damage to portions of a stent adjacent to a depot. Therefore, it may be desirable to couple a marker within a depot in an undeformed or substantially undeformed state through deformation of the stent adjacent to the depot.

In some embodiments, a stent may include a radiopaque marker disposed in a depot in a portion of the stent. The marker may be coupled to the stent at least partially by an interference fit between the marker and a deformed portion of the stent adjacent to the depot. In an embodiment, the marker may be undeformed or substantially undeformed after being coupled to the stent. In one embodiment, the deformed portion of the stent within the depot may include deformable projections adapted to deform when the marker is disposed in the depot. The projections may include ridges that are parallel, perpendicular, or between parallel and perpendicular to a cylindrical axis of the depot.

Figure 9A:
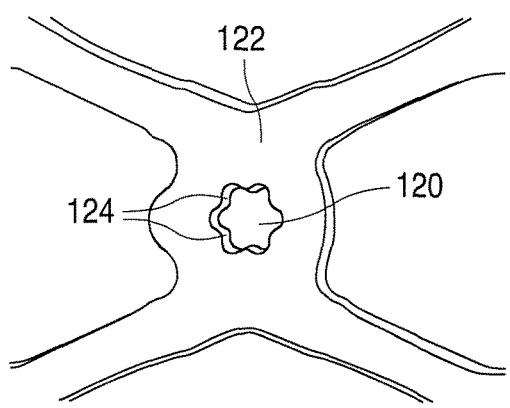
FIG. 9A depicts a portion of a stent with a depot including ridges.
Figure 9B:
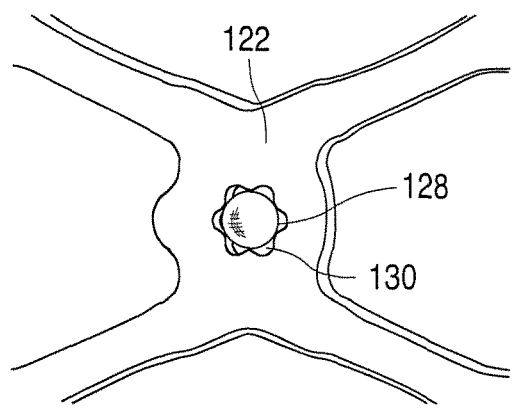
FIG. 9B depicts a spherical marker disposed within the depot of FIG. 9A.

FIG. 9A depicts a portion of a stent pattern with a depot 120 in a spider region 122. Depot 120 has ridges 124. FIG. 9B depicts a spherical marker 128 disposed within depot 120 of FIG. 9A. Marker 128 is coupled by an interference fit between undeformed marker 128 and deformed ridges 124. Voids 130 are shown between ridges 124. In some embodiments, coupling of the marker within a depot may be facilitated by at least partially filling the void with polymeric coating material, as described above.

In other embodiments, a depot may have a cross-section different from a cross-section of the marker. In addition, a length across a portion of the depot may be less than a cross-section of a marker. When the marker is disposed with the depot, the portion of the stent may deform to change the cross-section of the depot to accommodate the marker. The deformation of the stent may create an interference fit between the marker and a portion of the surface of the stent within the depot. For a marker with a circular cross-section such as a sphere or cylinder, depots with non-circular cross-sections can be a variety of shapes such as oval, ellipsoid, rectangular, etc.

Figure 10A:
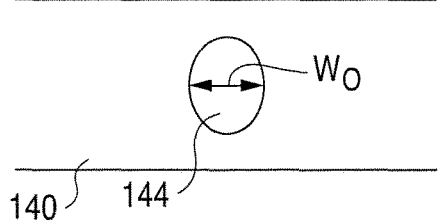
FIG. 10A depicts a portion of a stent with a depot having a non-circular cross-section.
Figure 10B:
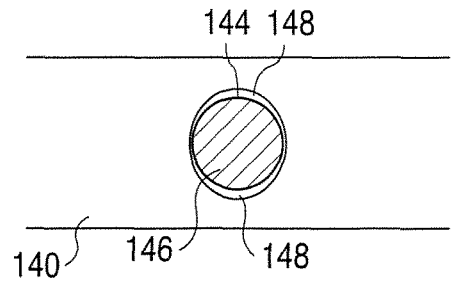
FIG. 10B depicts a portion of a stent with a spherical marker disposed within the depot in FIG. 10A.

FIG. 10A depicts an overhead view of a portion 140 of a stent with a depot 144 having a non-circular cross-section. Depot 144 has a width, $W_O$, that is less than a diameter $D_S$ of a spherical marker. FIG. 10B depicts portion 140 with a spherical marker 146 with diameter $D_S$ disposed within depot 144 from FIG. 10A. Portion 140 deforms to accommodate marker 146 to create an interference fit between marker 146 and a portion of the surface of portion 140 within depot 144. Voids 148 may be filled with a polymeric coating material, as described above.

As indicated above, positioning a marker within a depot may cause deformation in a portion of the stent adjacent to the depot. It may be desirable to increase the flexibility of the portion to reduce or eliminate damage to the stent as the portion deforms. In some embodiments, a surface of the portion adjacent to the depot may include a recess. The recess may facilitate deformation or increase the flexibility of the portion when the marker is disposed within the depot so as to facilitate coupling of the marker to the portion.

In one embodiment, the recess may be a groove in communication with the depot. The surface may include more than one groove of various widths and depths. For example, a groove may have a width that is less than 1%, 3%, 5%, 10%, 15%, 20%, or 20% of a diameter of a depot. Additionally, a groove may have a depth that is less than 1%, 3%, 5%, 10%, 15%, or 20% of a radial thickness of a strut that has the depot.

Figure 11A:
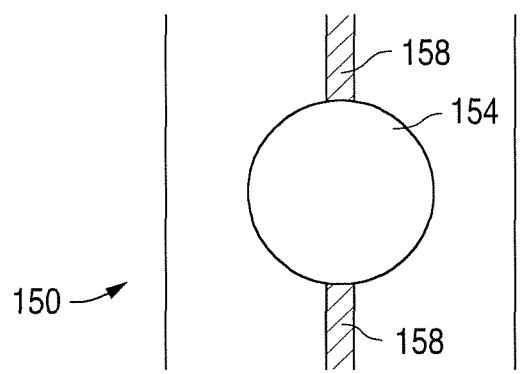
FIGS. 11A-B depict an overhead and side view of a portion of a stent with relief cuts adjacent to a marker depot.
Figure 11B:
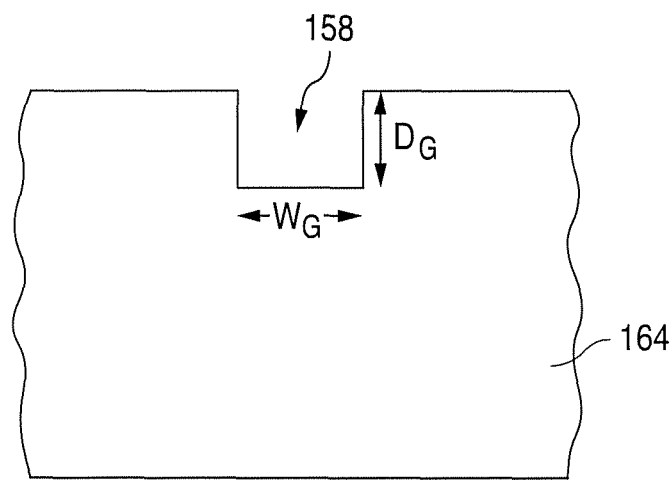

FIG. 11A depicts an overhead view of a portion 150 of a stent with a depot 154 for a marker. Portion 150 has grooves 158 in communication with the depot. FIG. 11B depicts a side view of grooves 158 facing an internal surface 164 of depot 154. Grooves 158 have depth $D_G$ and a width $W_G$. Grooves 158 are depicted with a rectangular cross-section, however, a groove may also have a rounded cross-section.

As indicated above, certain regions of polymeric struts tend to undergo significant deformation or strain during crimping and expansion. Such regions include curved or bent regions such as regions 14, 16, and 18 in FIG. 1 as well as regions where structural elements intersect such as portion 68 in FIG. 3. Thus, during stent deployment, the material surrounding a depot located in such regions may crack or stretch as stress is being applied to the expanding stent, and the marker may become dislodged. Straight or relatively straight portions such as section 19 in FIG. 1 tend to experience relatively low strain even during crimping and expansion.

Therefore, in some embodiments, it may be desirable or necessary to have a higher mass or thickness in regions with depots than regions without depots. The higher mass or thickness may reinforce the region which can at least partially compensate for the presence of the depot. A region can be reinforced with added mass of stent material so that it can adequately withstand the stress of crimping and expansion without significant distortion of the structural element in the region of the depot.

Furthermore, a high strain region tends to require a larger mass to compensate for the depot than a low strain region. An increase in mass of a stent increases the form factor of the stent, which is generally not desirable.

In certain embodiments, a stent may include a marker disposed within a depot in a portion of the stent. The stent may have regions with a lower strain than other higher strain regions when the stent is placed under an applied stress during use. The depot may be selectively positioned in a selected region of lower strain. The selected region of the structural element may be modified to have a higher mass or thickness than a region of lower strain without a marker so as to maintain the load-bearing capability of the selected region and to inhibit decoupling of the marker from the stent.

Figure 12A:
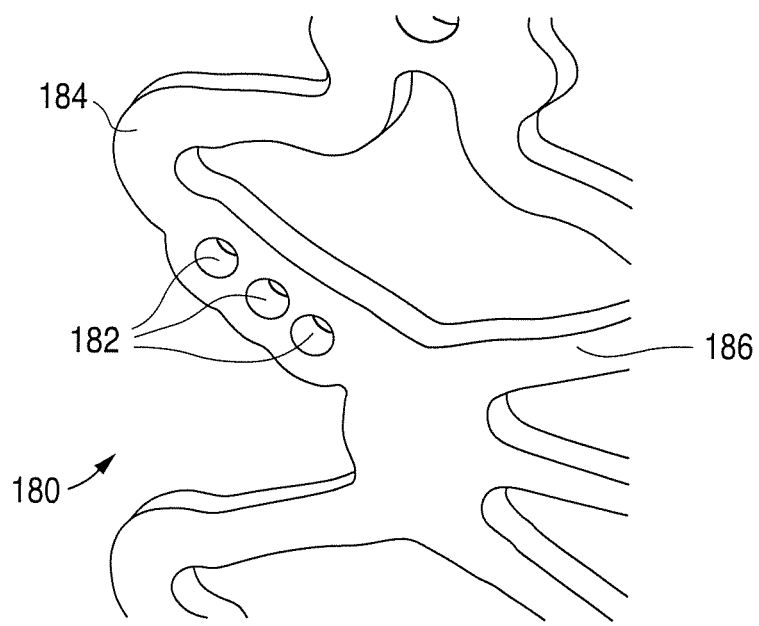
FIG. 12A depicts a portion of a stent with marker depots in a low strain region of a stent.
Figure 12B:
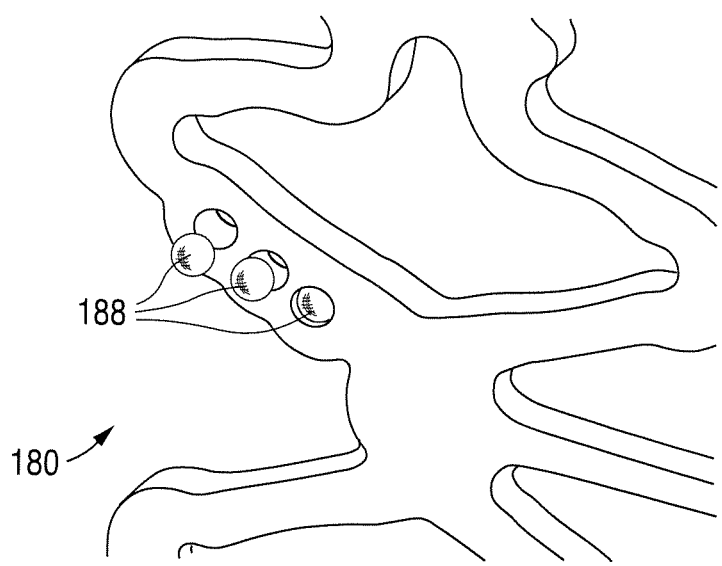
FIG. 12B depicts a portion of a stent with markers disposed in the depots of FIG. 12A.

FIG. 12A depicts a stent pattern 180 with depots 182 in portion 184, a low strain region of a stent. As shown in FIG. 12A, portion 184 is wider than a structural element 186 that has no depots. Portion 184 is wider or has more mass to maintain the structural integrity of the stent. FIG. 12B depicts spherical markers 188 disposed within depots 182. As shown in FIGS. 12A-B, one of the advantages of disposing markers in low strain regions such as portion 184 is that multiple markers can be accommodated. Thus, the visibility of the stent in enhanced.

Figure 13:
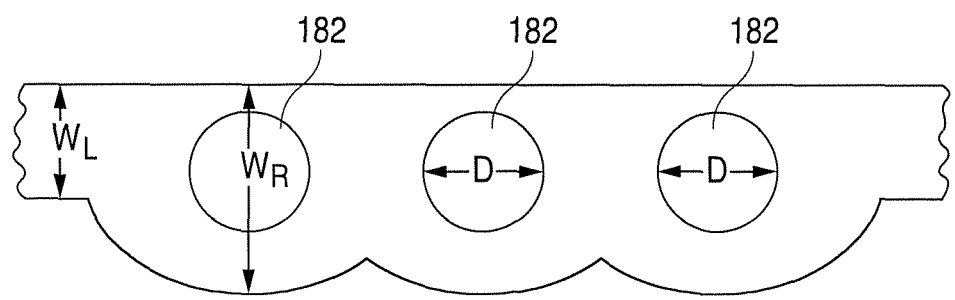
FIG. 13 depicts an overhead view of the portion of the stent in FIG. 12B.

FIG. 13 depicts an overhead view of portion 184 from FIGS. 12A-B. The part of portion 184 that is not reinforced has a width $W_L$ and a width of the reinforced part is $W_R$. $W_R$ may be greater than 120%, 140%, 160%, 180%, 200%, 220%, or 250% of $W_L$.

In certain embodiments, a spherical marker may additionally or alternatively be coupled within a depot with any suitable biocompatible adhesive. In one embodiment, the adhesive may include a solvent. The solvent may dissolve the polymer of the structural element within the depot to allow the marker within the depot to be coupled to the structural element. For markers that include a polymer, a solvent may also dissolve a portion of the marker. In another embodiment, the adhesive may include a solvent mixed with a polymer. The solvent or the solvent-polymer mixture may be applied to the structural element within the depot or the marker followed by disposing the marker within the depot. The solvent may then be removed through evaporation. Evaporation may be facilitated by, for example, heating the structural element in an oven or by some other method.

Representative examples of solvents may include, but are not limited to, chloroform, acetone, chlorobenzene, ethyl acetate, 1,4-dioxane, ethylene dichloride, 2-ethyhexanol, and combinations thereof. Representative polymers may include biostable and biodegradable polymers disclosed herein that may be dissolved by the selected solvent.

In other embodiments, adhesives may include, but are not limited to, thermosets such as, for example, epoxies, polyesters and phenolics; thermoplastics such as, for example, polyamides, polyesters and ethyl vinyl acetate (EVA) copolymers; and elastomers such as, for example, natural rubber, styrene-isoprene-styrene block copolymers, and polyisobutylene. Other adhesives include, but are not limited to, proteins; cellulose; starch; poly(ethylene glycol); fibrin glue; and derivatives and combinations thereof.

Mixtures of solvents and another substance can be used to form adhesives. In some embodiments, mixtures of water and sugar such as, for example, mixtures of water and sucrose, can be used as an adhesive. In other embodiments, mixtures of PEG, or derivatives thereof, can be mixed with a suitable solvent to form an adhesive. Suitable solvents for PEG, or derivatives thereof, include, but are not limited to, water, ethanol, chloroform, acetone, and the like.

In other embodiments, the marker can be coupled to the structural element by a thermal weld. Prior to disposing the marker in the structural element, a metallic marker may be heated to a temperature that can melt at least a portion of the polymer of the structural element. A marker including a polymer can be heated to a temperature at or above its melting temperature prior to disposing the marker in the depot.

Furthermore, the markers may be coupled to any desired location on a stent. In some embodiments, it may be advantageous to limit the placement of a marker to particular locations or portions of surfaces of a stent. For example, it may be desirable to couple a marker at a sidewall face of a structural element to reduce or eliminate interference with a lumen wall or interference with blood flow, respectively. To delineate just the margins of the stent so that the physician may see its full length, markers can be placed only at the distal and proximal ends of the stent.

Additionally, a device such as a stent may typically include two or more markers coupled to various locations of the stent. The markers may be distributed in a manner that facilitates visualization of the stent during and after implantation. For instance, the markers may be distributed circumferentially and longitudinally throughout a stent pattern.

As indicated above, a stent may include a biostable and/or a biodegradable polymer. The biodegradable polymer may be a pure or substantially pure biodegradable polymer. Alternatively, the biodegradable polymer may be a mixture of at least two types of biodegradable polymers. The stent may be configured to completely erode away once its function is fulfilled.

In certain embodiments, the marker may be biodegradable. It may be desirable for the marker to degrade at the same or substantially the same rate as the stent. For instance, the marker may be configured to completely or almost completely erode at the same time or approximately the same time as the stent. In other embodiments, the marker may degrade at a faster rate than the stent. In this case, the marker may completely or almost completely erode before the body of the stent is completely eroded.

Furthermore, a radiopaque marker may be composed of a biodegradable and/or biostable metal. Biodegradable or bioerodable metals tend to erode or corrode relatively rapidly when exposed to bodily fluids. Biostable metals refer to metals that are not biodegradable or bioerodable or have negligible erosion or corrosion rates when exposed to bodily fluids. In some embodiments, metal erosion or corrosion involves a chemical reaction between a metal surface and its environment. Erosion or corrosion in a wet environment, such as a vascular environment, results in removal of metal atoms from the metal surface. The metal atoms at the surface lose electrons and become charged ions that leave the metal to form salts in solution.

Additionally, it is desirable to use a biocompatible biodegradable metal for a marker. A biocompatible biodegradable metal forms erosion products that do not negatively impact bodily functions.

In one embodiment, the radiopaque marker may be composed of a pure or substantially pure biodegradable metal. Alternatively, the marker may be a mixture or alloy of at least two types of metals. Representative examples of biodegradable metals for use in a marker may include, but are not limited to, magnesium, zinc, and iron. Representative mixtures or alloys may include magnesium/zinc, magnesium/iron, zinc/iron, and magnesium/zinc/iron. Radiopaque compounds such as iodine salts, bismuth salts, or barium salts may be compounded into the metallic biodegradable marker to further enhance the radiopacity.

Representative examples of biostable metals can include, but are not limited to, platinum and gold.

In some embodiments, the composition of the marker may be modified or tuned to obtain a desired erosion rate and/or degree of radiopacity. For example, the erosion rate of the marker may be increased by increasing the fraction of a faster eroding component in an alloy. Similarly, the degree of radiopacity may be increased by increasing the fraction of a more radiopaque metal, such as iron, in an alloy. In one embodiment, a biodegradable marker may be completely eroded when exposed to bodily fluids, such as blood, between about a week and about three months, or more narrowly, between about one month and about two months.

In other embodiments, a radiopaque marker may be a mixture of a biodegradable polymer and a radiopaque material. A radiopaque material may be biodegradable and/or bioabsorbable. Representative radiopaque materials may include, but are not limited to, biodegradable metallic particles and particles of biodegradable metallic compounds such as biodegradable metallic oxides, biocompatible metallic salts, gadolinium salts, and iodinated contrast agents.

In some embodiments, the radiopacity of the marker may be increased by increasing the composition of the radiopaque material in the marker. In one embodiment, the radiopaque material may be between 10% and 80%; 20% and 70%; 30% and 60%; or 40% and 50% by volume of the marker.

The biodegradable polymer in the marker may be a pure or substantially pure biodegradable polymer. Alternatively, the biodegradable polymer may be a mixture of at least two types of biodegradable polymers. In one embodiment, the composition of the biodegradable polymer may be modified to alter the erosion rate of the marker since different biodegradable polymers have different erosion rates.

A biocompatible metallic salt refers to a salt that may be safely absorbed by a body. Representative biocompatible metallic salts that may used in a marker include, but are not limited to, ferrous sulfate, ferrous gluconate, ferrous carbonate, ferrous chloride, ferrous fumarate, ferrous iodide, ferrous lactate, ferrous succinate, barium sulfate, bismuth subcarbonate, bismuth potassium tartrate, bismuth sodium iodide, bismuth sodium tartrate, bismuth sodium triglycollamate, bismuth subsalicylate, zinc acetate, zinc carbonate, zinc citrate, zinc iodate, zinc iodide, zinc lactate, zinc phosphate, zinc salicylate, zinc stearate, zinc sulfate, and combinations thereof. The concentration of the metallic salt in the marker may be between 10% and 80%; 20% and 70%; 30% and 60%; or 40% and 50% by volume of the marker.

In addition, representative iodinated contrast agents may include, but are not limited to acetriozate, diatriozate, iodimide, ioglicate, iothalamate, ioxithalamate, selectan, uroselectan, diodone, metrizoate, metrizamide, iohexol, ioxaglate, iodixanol, lipidial, ethiodol, and combinations thereof. The concentration of an iodinated contrast agent in the marker may be between 5% and 80%; 20% and 70%; 30% and 60%; or 40% and 50% by volume of the marker.

The composition of metallic particles may include at least those biodegradable metals discussed above as well as metallic compounds such as oxides. The concentration of metallic particles in the marker may be between 10% and 80%; 20% and 70%; 30% and 60%; or 40% and 50% by volume of the marker. Additionally, individual metallic particles may be a pure or substantially pure metal or a metal compound. Alternatively, individual metallic particles may be a mixture of at least two types of metals or metallic compounds. Individual metallic particles may also be a mixture or an alloy composed of at least two types of metals.

In certain embodiments, the metallic particles may be metallic nanoparticles. A "nanoparticle" refers to a particle with a dimension in the range of about 1 nm to about 100 nm. A significant advantage of nanoparticles over larger particles is that nanoparticles may disperse more uniformly in a polymeric matrix, which results in more uniform properties such as radiopacity and erosion rate. Additionally, nanoparticles may be more easily absorbed by bodily fluids such as blood without negative impact to bodily functions. Representative examples of metallic particles may include, but are not limited to, iron, magnesium, zinc, platinum, gold, and oxides of such metals.

In one embodiment, the composition of different types of metallic particles in the mixture as well as the composition of individual particles may be modified to alter erosion rates and/or radiopacity of the marker. In addition, the ratio of polymer to metallic particles may be modified to alter both the erosion rate and radiopacity.

A marker may be fabricated by methods including, but not limited to, molding, machining, assembly, or a combination thereof. All or part of a metallic or polymeric marker may be fabricated in a mold or machined by a method such as laser machining.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:
1. A bioabsorbable stent comprising:
   a single cylindrical or spherical radiopaque marker disposed in a depot in a portion of the stent, wherein the marker comprises a sufficient radiopacity to be imaged by an imaging technique, wherein a gap between the marker and an internal surface of the depot is at least partially filled with a polymeric material, the depot extends partially through the portion of the stent such that only one of a luminal side and an abluminal side of the depot is open, and the stent is fabricated from a polymer and the marker is a pure metal or a mixture or alloy of at least two types of metals for allowing the marker to be imaged by the imaging technique.

2. A bioabsorbable stent comprising:

two or more radiopaque markers each disposed in a depot in a portion of the stent, wherein each depot holds one marker and the markers comprise a sufficient radiopacity to be imaged by an imaging technique, wherein the two or more markers are in circumferentially offset positions;

at least some gaps between the markers and internal surfaces of the depots are at least partially filled with a polymeric material, each depot extends partially through the portion of the stent where the depot is located such that only one of a luminal side and an abluminal side of the depot is open, and the stent is fabricated from a polymer and the markers are a pure metal or a mixture or alloy of at least two types of metals for allowing the markers to be imaged by the imaging technique.

3. A bioabsorbable stent comprising:

a cylindrical radiopaque marker disposed in a cylindrical depot in a portion of the stent, wherein the marker comprises a sufficient radiopacity to be imaged by an imaging technique, wherein the marker is on the portion that connects two bending elements of the stent at an apex of each bending element, the apices pointing toward and aligned with one another, a gap between the marker and an internal surface of the cylindrical depot is at least partially filled with a polymeric material, and the stent is fabricated from a polymer including poly(L-lactide-co-caprolactone) and the marker is a mixture or alloy of at least two types of metals for allowing the marker to be imaged by the imaging technique.

* * * * *